United States Patent [19]

Frech et al.

[11] Patent Number: 4,772,259
[45] Date of Patent: Sep. 20, 1988

[54] HYPERBARIC OXYGENATION APPARATUS AND METHODS

[75] Inventors: Gary Frech, Taylorsville; John M. Daniels, Salt Lake City, both of Utah

[73] Assignee: Ballard Medical Products, Midvale, Utah

[21] Appl. No.: 62,297

[22] Filed: Jun. 12, 1987

[51] Int. Cl.$^4$ ............................................. A61M 37/00
[52] U.S. Cl. ...................... 604/23; 604/293
[58] Field of Search ...................... 604/23–25, 604/293; 128/1 B, 38, 65, 66, 368, 370, 375, DIG. 20

[56] References Cited

U.S. PATENT DOCUMENTS

| | | |
|---|---|---|
| 2,168,611 | 8/1939 | Thompson . |
| 3,450,450 | 6/1969 | Hopkins et al. . |
| 3,712,298 | 1/1973 | Snowden et al. . |
| 3,744,491 | 7/1973 | Fischer . |
| 4,003,371 | 1/1977 | Fischer .............................. 604/293 |
| 4,211,223 | 7/1980 | LoPiano ................................ 604/23 |
| 4,236,513 | 12/1980 | LoPiano . |
| 4,509,513 | 4/1985 | Lasley . |
| 4,691,695 | 9/1987 | Birk et al. ........................ 128/375 |

FOREIGN PATENT DOCUMENTS

114443 12/1941 Australia .
317900 12/1919 Fed. Rep. of Germany .

OTHER PUBLICATIONS

Topox literature, The Topox Corporation, Jersey City, N.J.

Oxycure literature, Concord Laboratories, Inc., Keene, N.H.

B & F Medical Products, Inc. literature #64390, Toledo, Ohio.

Primary Examiner—Stephen C. Pellegrino
Assistant Examiner—Ralph Lewis
Attorney, Agent, or Firm—Lynn G. Foster

[57] ABSTRACT

A novel hyperbaric oxygenation apparatus, and related methods, the apparatus comprising a chamber in the form of a disposable inflatable bag of impervious inexpensive synthetic resinous material which can be used at any desired location, such as a hospital, a home or other site where oxygen can be appropriately made available. The pressure of the oxygen in the collapsible bag is pulsated between maximum and minimum positive values. The patient cyclically experiences first a medicinal increase in the blood gas levels in the limb under treatment with a corresponding restricted blood flow and, thereafter, a progressive return to normal blood flow rates in the limb of the patient as the pressure in the chamber changes from maximum to minimum positive pressure. A respirator, normally used for intubated respiratory patients, in conjunction with a single oxygen influent/effluent port in hyperbaric oxygenation apparatus is efficacious to provide the oxygen and generate the desired pressure variations. Cuff inversion under positive pressure is prevented by anti-blowout structure. Pressure loss between the outside of the cuff and the inside of the bag is also prevented. A simplified proximal end is provided for the hyperbaric oxygenation apparatus.

3 Claims, 4 Drawing Sheets

HYPERBARIC OXYGENATION APPARATUS AND METHODS

FIELD OF INVENTION

The present invention relates generally to oxygenation of a limb of a medical patient and more particularly to novel hyperbaric oxygenation apparatus, and related methods, by which a selected limb of a medical patient is effectively oxygenated.

PRIOR ART

While external hyperbaric oxygen chambers have been used over the years to treat the wounds, sores, etc. of medical patients, certain problems have persisted including inadvertent loss of pressure during hyperbaric treatment, typically caused by inversion (pressure blowout) of a limb-engaging cuff at the proximal end of such hyperbaric chambers.

Patents known to the applicants are:

| | |
|---|---|
| U.S. Pat. No. 2,168,611 | U.S. Pat. No. 2,385,683 |
| U.S. Pat. No. 3,450,450 | U.S. Pat. No. 3,478,738 |
| U.S. Pat. No. 3,712,298 | U.S. Pat. No. 3,744,491 |
| U.S. Pat. No. 3,749,091 | U.S. Pat. No. 3,768,467 |
| U.S. Pat. No. 4,236,513 | U.S. Pat. No. 4,328,799 |
| U.S. Pat. No. 4,467,798 | U.S. Pat. No. 4,474,571 |
| U.S. Pat. No. 4,509,513 | West German 317,900 |
| British 114,443 | |

To the extent that the above-identified patents are relevant, they are individually and collectively of general interest only.

In the past, it has been advocated that expensive and complex equipment be fabricated for one specific purpose, i.e. to control the amount of oxygen delivered to and the pressure levels within a hyperbaric chamber. It has also been the common thinking within the medical field that the interior of hyperbaric chambers should be either maintained at a constant relatively high pressure or cycled between a maximum positive and a minimum vacuum pressure. The medical profession has retained a clear preference for massive, single locaton, expensive, iron lungtype hyperbaric chambers. In contrast the medical profession has been basically dissatisfied with previously proposed disposable hyperbaric chambers. One of the major reasons for the indicated preference is that the proximal sleeve of such prior disposable hyperbaric chambers tends to roll back upon itself (invert) during use under positive pressure applied within the hyperbaric chamber causing a loss of pressure which defeats the intended purpose of the chamber.

BRIEF SUMMARY AND OBJECTS OF THE INVENTION

In brief summary, the present invention overcomes or substantially alleviates the aforementioned prior art problems and provides a novel hyperbaric oxygenation apparatus, and related methods, the apparatus comprising a chamber in the form of a disposable inflatable bag of impervious inexpensive synthetic resinous material which can be used at any desired location, such as a hospital, a home or other site where oxygen can be appropriately made available and which solves the aforementioned pressure loss problem caused by inversion or blowout of the cuff or sleeve disposed at the proximal end of prior hyperbaric chambers. The present invention also prevents pressure loss between the outside of the cuff and the inside of the bag at the proximal end of the apparatus.

The present hyperbaric oxygenation invention, therefore, provides for: an inexpensive and reliable hyperbaric oxygenation apparatus and related methods and reliable retention of the desired pressure values and variations thereof within the oxygenation apparatus. A simplified proximal end for a hyperbaric oxygenation apparatus is provided.

With the foregoing in mind, it is a primary object of the present invention to provide novel hyperbaric oxygenation apparatus and related methods.

A further important object of the present invention is to provide a novel hyperbaric oxygenation apparatus and related methods which overcome or substantially alleviate the aforementioned problems of the prior art.

It is an additional significant object of the present invention to provide a novel and reliable hyperbaric oxygenation apparatus comprising a chamber in the form of a disposable inflatable bag of impervious inexpensive synthetic resinous material.

An additional object of significance is the provision of novel structure by which the aforementioned pressure loss problem, caused by inversion or blowout of the cuff or sleeve disposed at the proximal end of the bag, is solved.

A further dominant object of the present invention is the provision of novel structure by which pressure loss between the outside of the cuff and the inside of the bag at the proximal end of a hyperbaric oxygenation apparatus.

Another object of consequence is the provision of a simplified proximal end for a hyperbaric oxygenation apparatus.

These and other objects and features of the present invention will be apparent from the detailed description taken with reference to the accompanying drawings.

DETAILED DESCRIPTION OF THE ILLUSTRATED EMBODIMENTS

Figures 1, 4:
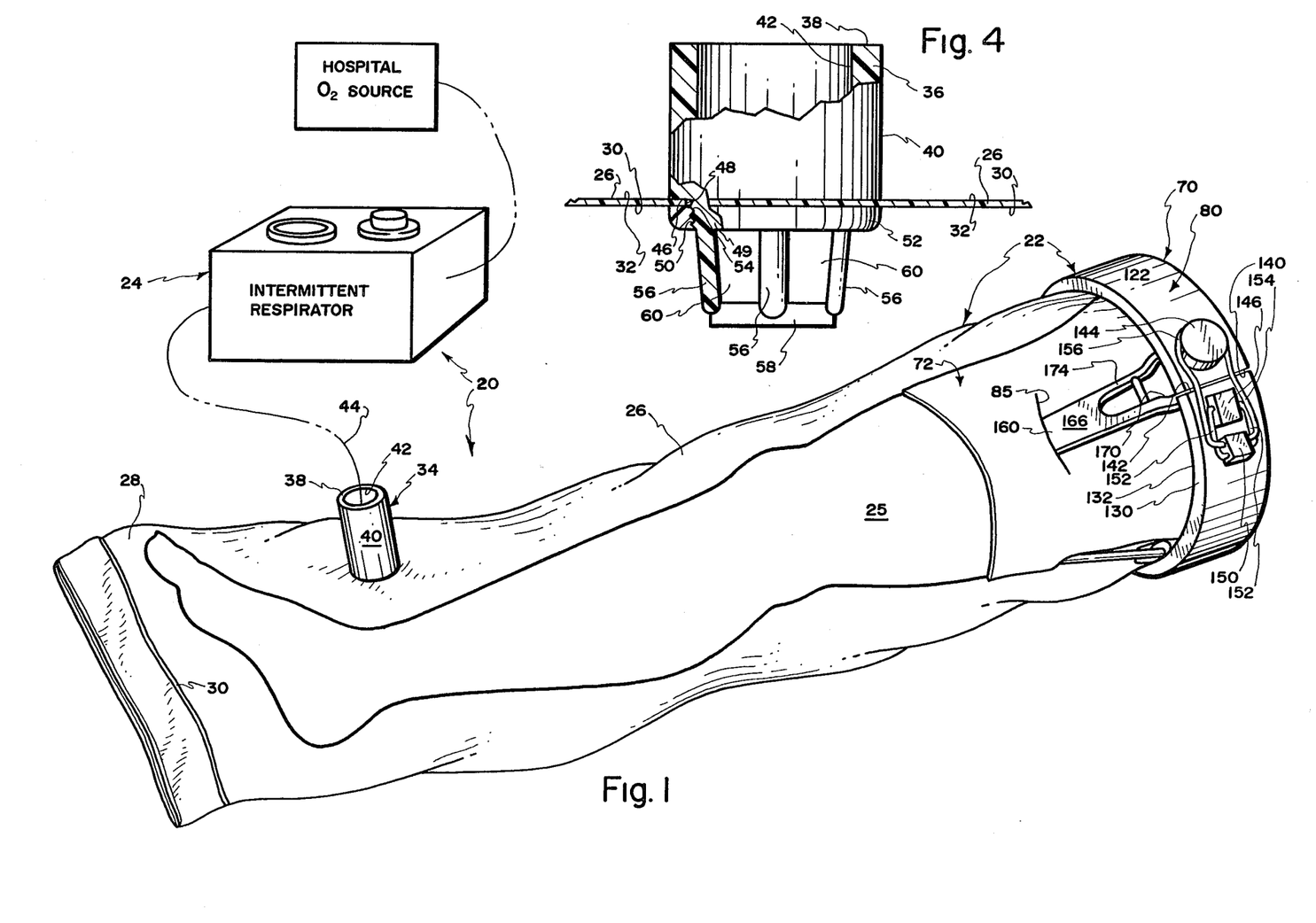
FIG. 1 is a perspective representation illustrating a presently preferred hyperbaric oxygenation apparatus according to the present invention installed upon a limb of a medical patient.
FIG. 4 is a side elevation of the presently preferred oxygen port lounded upon the bag of the apparatus of FIG. 1.

Reference is now made to the drawings wherein like numerals are used to designate like parts throughout. FIG. 1 illustrates, in perspective, a presently preferred hyperbaric oxygenation system, generally designated 20. System 20 comprises a hyperbaric oxygenation chamber apparatus, generally designated 22 and an intermittent respirator, generally designated 24, of the type generally used in resiratory for intubated patients. The apparatus 22 is illustrated as being operatively installed upon a leg 25 of a patient.

The hyperbaric apparatus 22 comprises a collapsible and inflatable bag 26 of gas impervious synthetic resinous film, such as by-axial polyvinyl chloride. The bag 26 is illustrated as being in the form of a length of cylindrical sleeve stock. The distal end 28 is closed and hermetically sealed. A heat seal seam 30 is presently preferred for purposes of closing and sealing the distal end 28 of the tubular bag 26. Utilization of heat sealing is an inexpensive, readily available technique which provides for reliable impervious closure of the distal end of the bag 26. The closure 30 also facilitates convenience in packaging and shipping the apparatus 22.

The bag 26 is preferably formed from single ply material and defines a hollow interior 32 (FIG. 3) sized to comfortably receive the limb 25 for oxygenation. The bag 26 is illustrated as having a wall thickness 32 which is substantially uniform throughout.

The hyperbaric mechanism 22 comprises a single rigid oxygen port 34 (FIGS. 1 and 4) which accommodates both influent and effluent flow of oxygen into and from the hollow interior 30 of the bag 26. The port 34 comprises an annular outwardly projecting wall 36 which terminates in an elevated blunt edge 38. The annular wall 36 is illustrated as being of uniform thickness disposed external of the bag 26 and defined by an outside cylindrical surface 40 and an interior cylindrical surface 42 where a fluid communicating tube 44, diagrammatically illustrated in FIG. 1, is connected in a conventional manner. Preferably the material from which the oxygen port 34 is fabricated is a satisfactory synthetic resinous material in shape-retaining rigid form, such as medical grade injection molded polyurethane. The wall 36 is reduced in its outside diameter at surface 40 at shoulder 46, which shoulder contiguously engages the bag 26. The shoulder 46 is sized so as to corresponds in size and be aligned with an aperture 48 formed in the bag 26. The shoulder 46 merges with a projection 49 comprising threads 50, disposed essentially within the hollow interior of the bag 26 adjacent to the aperture 48. A ring 52 comprising a threaded aperture 54 is tightened upon the threads 50 and against the bag 26 to compressively hold the bag 26 adjacent to the aperture 48 between the shoulder 46 and the ring 52, as best illustrated in FIG. 4.

The projection 49 merges into a plurality of spaced inwardly extending arms 56, the respective distal ends of which are integrally secured to a flat baffle plate 58. Thus, air entering the bag 26 through the port 34 will pass along the bore 42, against the baffle plate 58 and into the hollow interior 30 of the bag 26 transversely of the port 34 through the openings 60 between the spaced arms 56. Accordingly, the air is prevented from directly striking the limb 25 of the patient.

The hyperbaric apparatus 22 also comprises a proximal end assembly, generally designated 70, by which the proximal end of the mechanism 22 is releasably hermetically sealed to the limb of the patient undergoing oxygenation treatment in such a way as to prevent inadvertent, undesired loss of positive pressure from the interior 38 of the bag 26, as herinafter more fully explained.

The proximal end assembly 70 comprises an elastic tapered sleeve or cuff, generally designated 72, a ring 74 (FIG. 3), which is secured to the proximal end of the bag 26 as hereinafter more fully explained, a collar, generally designated 76, a plurality of separate cuff-retaining struts, each generally designated 78, and a compression collar clamp, generally designated 80.

Figure 3:
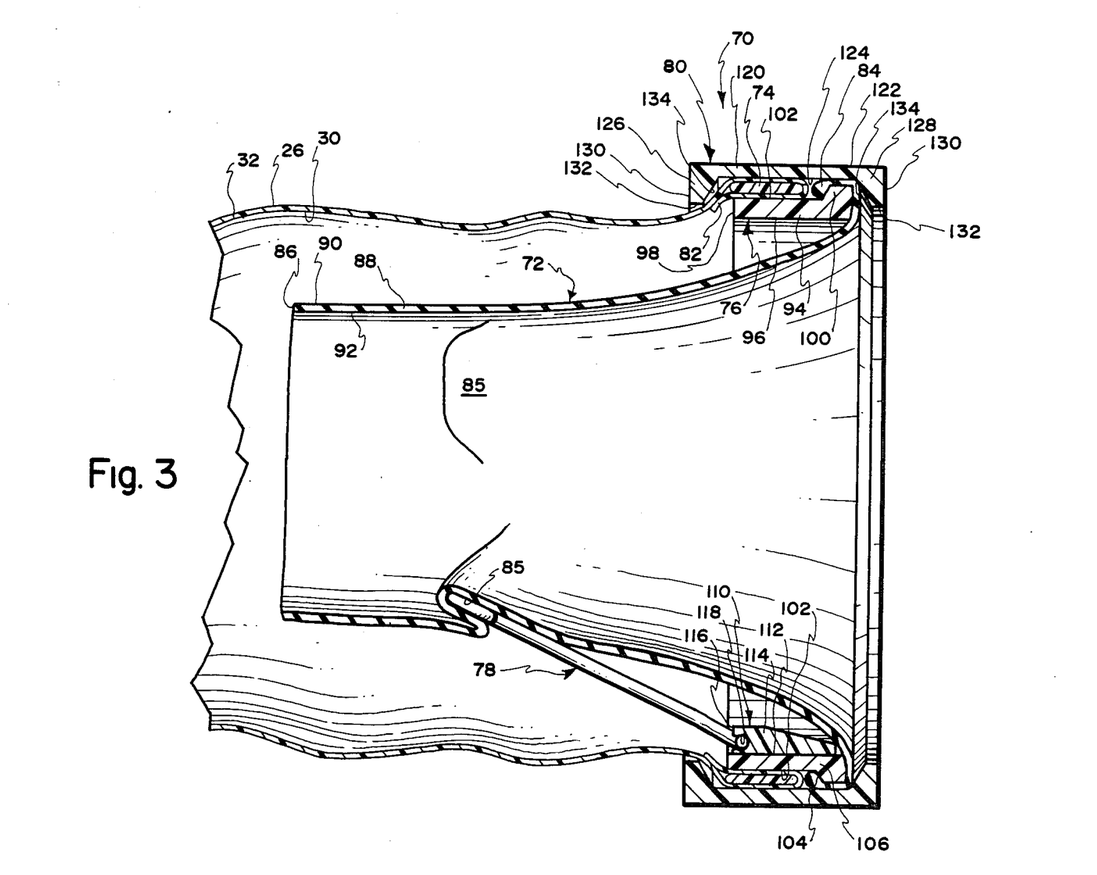
FIG. 3 is an enlarged fragmentary cross-sectional view of the assembled proximal end of the apparatus of FIG. 1.

The bag 26, illustrated as being a cylindrical sleeve, is secured to the ring 74 by interposing a suitable adhesive between the surfaces of the ring 74 and the bag wall 32 to be overlapped and wrapping the proximal end 82 of the bag around the ring 74, as best illustrated in FIG. 3. The wrapping is illustrated as being first over the top surface of the ring 74, then around the trailing edge of the ring 74 and thence along the bottom surface of the ring 74. Thus, the proximal end 82 of the bag wall 32 is in the form of an annular loop which encases the ring 74. The ring 74 is illustrated as being a flat band preferably rigid, formed from a suitable synthetic resinous material, such as polyurethane using conventional injection molding techniques.

The cuff or sleeve 72 is illustrated as being tapered convergently from an annular enlarged trailing end lip 84 thereof to the distal blunt edge 86 thereof, when in an unstressed state. Preferably, the sleeve or cuff 72 extends for a considerably greater distance than is illustrated in the Figures with a continuing convergent conical taper back to front. At the time of installation of the apparatus 22 upon the limb 25 of the patient, the diameter of the limb adjacent to the proximal end assembly 70 is sized and coordinated with the enlarging diametral dimension of the cuff 72. A cut line is made with a suitable instrument to form blunt edge 86.

The diametral dimension at edge 86 is selected to be slightly smaller than the diametral dimension of the limb 25 at the site where the cuff 72 is to be contiguously located. In that way, insertion of the limb through the cuff 72 will enlarge the previously unstressed diametral dimension of the cuff at and near the blunt edge 86 so that the sleeve 72 will exert a relatively wide compressive radial force upon the limb 25. The cuff 72 is illustrated as comprising a thin wall 88 having a uniform thickness throughout and comprising outside wall surface 90 and interior wall surface 92.

Intermediate the edge 86 and the lip 84 of the cuff 72 are three pockets 85 integrally formed in the cuff 72. Each pocket 85 is, therefore, integral with the wall 88 of the cuff 72 and has an internal longitudinal length and an internal width selected to accommodate receipt of the respective support struts 78 as hereinafter more fully explained. The pockets are illustrated as being disposed at 120 degree intervals around the sleeve 72.

The collar 76, of the proximal end assembly 70, is preferably formed of rigid synthetic resinous material, such as polyurethane, using conventional injection molding techniques. The collar 76 comprises a generally annular configuration comprising a wall 94. The wall 94 comprises an internal cylindrical surface 96 a blunt leading edge 98 and a chamfered trailing edge 100. The wall 96 also comprises an exterior cylindrical surface 102, which is longitudinally stepped at angular shoulder 104 to form an enlarged trailing annular lip 106. The diameter of the external surface 102 is slightly smaller than the diameter of the inside surface of the ring 74. Thus, the ring 74 with the proximal end 82 of the bag wall 32 wrapped therearound may be snugly force-fit over the surface of 102 in the manner best illustrated in FIG. 3.

The outside diameter of the trailing flange or lip 106 is substantially greater than the at rest diameter of the trailing lip 84 of the cuff or sleeve 72. The proximal end of the sleeve 72 is assembled into the position illustrated in FIG. 3 by diametrally manually stretching the diameter of the trailing lip 84 and the adjacent wall 82 of the cuff 72, while inverting the lip 84 upon the sleeve wall 88 and forcing the lip 84 over the annular lip 106 and against the surface 102, as shown in FIG. 3. In this position, the memory of the material from which the ring or enlarged lip 84 and the wall 88 of the cuff 72 is made will exert a compressive stress upon the collar 76 thereby holding the proximal end of the cuff 72 in the described stretched condition.

The collar 76 also comprises, as illustrated, three strutretaining clips, each generally designated 110. Each clip 110 is secured to the inside surface 96 of the collar 76, at interface 112, using a suitable adhesive, bonding agent or the like. Each clip comprises a body of material 114 which comprises a forwardly exposed edge 116, in which is disposed a generally transverse keyhole-shaped slot 118, for purposes yet to be explained.

Each strut 78 is preferably of one-piece injection molded manufacture comprising a suitable synthetic resinous material, such as rigid polyurethane. Each strut 78 comprises a wide arcuate distal shoe or foot 160 which comprises a thin arcuate wall having a curvature substantially the same as the curvature of the cuff wall 88. The wall forming the arcuate shoe 160 is illustrated as being of uniform thickness and spans transversely between one rounded side edge 162 to a second rounded side edge 164. The distance transversely spanned by the shoe 160 between side edges 162 and 164 is substantially equal to the transverse width of the pocket 85 into which the foot 160 is placed in the assembled condition, as best illustrated in FIG. 3. Thus, the wide foot 160 is situated entirely within the associated pocket 85 and is there retained against inadvertent separation. Preferably this strut placement occurs after sleeve 72 is mounted upon collar 76 and before ring 74 is positioned upon collar 76.

Each strut 78 also comprises a load-transmitting central essentially linear bar 166. The central bar 166 is integrally joined, at site 168, to the foot 160 and comprises a length selected to be substantially that distance between the opening to the associated pocket 85 and the base of the keyway slot 118 in the associated clip. The trailing end of the central bar 166 comprises an aperture 170, which is bridged at the proximal end by a transverse bridge 172. Bridge 172 is integral with parallel wall segments 174 and 176. The aperture 170 and the bar 172 are sized so that the keyhole shaped slot 118 of the associated clip 110 will accommodate an interference-fit acceptance of the bar 172 in the fully assembled condition, as illustrated in FIG. 3.

It has been found that by utilization of the struts 78 placed diagonally, as illustrated in FIG. 3, between the sleeve pockets 85 and the clips 110, longitudinal and inwardly directed radial forces are exerted upon the cuff 72 which prevent inversion or blowout of the cuff and thus prevent undesired pressure loss at the proximal end of the apparatus during use.

Once the assembled proximal bag end 82 and ring 74 are placed in the position illustrated in FIG. 3, the struts 78 are in place and the enlarged lip 84 of the cuff 72 is likewise placed in its stretched inverted posture over the radially enlarged flange 106, the collar clamp 80 is ready for placement at the proximal end 70.

The collar clamp 80 comprises an annular wall 120 which is split at one location and has a front-to-back dimension which is greater than the front-to-back dimension of the collar 94. The wall 120 comprises an exposed external cylindrical surface 122 and an internal cylindrical surface 124, the longitudinal distance of which is slightly greater than the longitudinal dimension of the collar wall 94. The wall 120 is interposed between and integral with inwardly directed radially disposed front and back flanges 126 and 128. The flange 126 comprises a leading blunt edge surface 130, a cylindrical shoulder 132 and an annular diagonally directed surface 134, which merges with surface 124. The trailing flange 128 is similarly constructed and numbered, though of opposite hand.

The diameter of the inner surface 124 of the wall 120 is selected so that wall 120 is caused to exert radial pressure upon the proximal end 82 of the bag 26, the ring 74 and the trailing lip 84 and adjacent wall 88 of the cuff 72 to retain the assembled condition once the proximal end assembly 70 is fully assembled and clamped.

Figure 2:
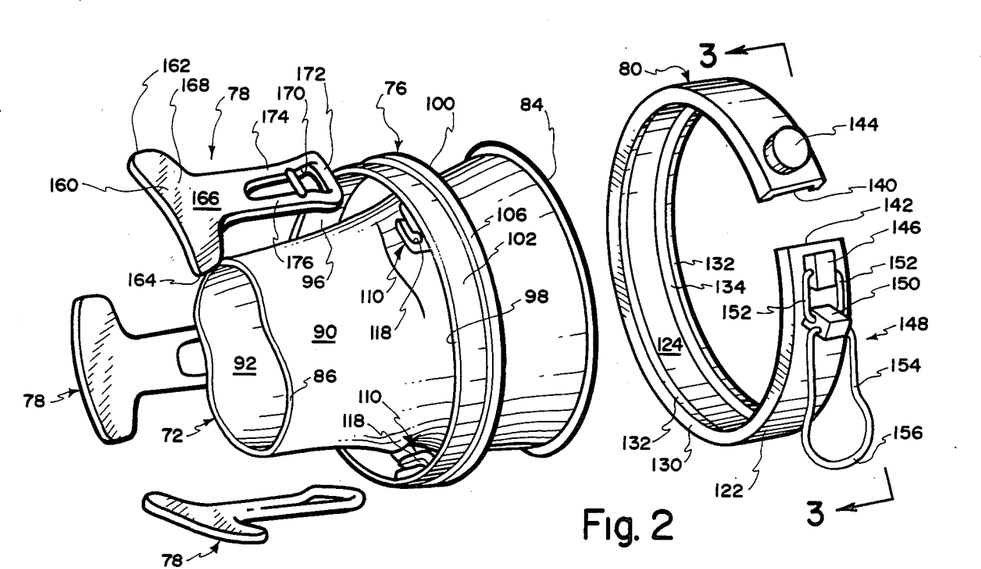
FIG. 2 is a fragmentary exploded perspective of the proximal end of the apparatus of FIG. 1.

The collar clamp 80 is axially slit to form ring edges 140 and 142. See FIG. 2. A male annular button 144 is integrally secured to the exterior surface 122 of the wall 120 adjacent the blunt slit edge 140, while a rectangular clamp mounting abutment block 146 is integrally secured to the external surface 122 of the wall 120 adjacent the slit edge 142. The block 146 carries a toggle clamp 148. The toggle clamp comprises a toggle block 150, which is secured by parallel embedded wires 152 to the mounting block 46. A latch wire 154 having an enlarged loop 156 is also anchored in the toggle block 150. Accordingly, the collar clamp 80 may be manually diametrically enlarged and axially superimposed upon the otherwise assembled portions of the proximal end assembly 70 until the collar clamp 80 is in accurate radial alignment therewith. The enlarged loop 156 is placed over the cylindrical button 144 and the toggle mechanism 148 manually closed into its locked condition, as best illustrated in FIG. 1. This will compressively radially hold the assembly 70 in its assembled relationship.

It has been discovered that by pulsating the pressure and delivery of oxygen to the bag 26 encapsulating the limb 25 between maximum and minimum positive values, which may be selectively set for any given patient depending upon the health and condition of the patient, the patient cyclically experiences first a desirable increase in the blood gas levels accompanied restricted blood flow within the limb of the patient under treatment and thereafter a return to normal blood flow rates within said limb. Surprisingly, it has been found that utilization of an existing hospital or like respirator, normally for use with intubated respiratory patients, can be connected to the apparatus 22. Oxygen delivered from the respirator to the bag 26 cyclically first until the bag is entirely inflated and the internal pressure thereof is at a predetermined maximum positive value desirable for enhancement of blood gas levels in the patient and thereafter, with delivery of the oxygen temporarily terminated by the respirator, oxygen is slowly bled from the bag through the port 34 until the bag is partially deflated and the minimum desired positive oxygen pressure within the bag is obtained. Thereafter, the cycle is repeated.

While any suitable respirator with appropriate capacity can be used, it is presently preferred that the Bird Mark Seven be used. The Bird Mark Seven is a positive pressure, positive-cycled, assistor-controller (pneumatic) ventilator available from the Bird Corporation. The pressure settings available on the Bird Mark Seven range from 0 to 60 cm water pressure at 50 psi. Cycle times may be set as desired.

Figure 5:
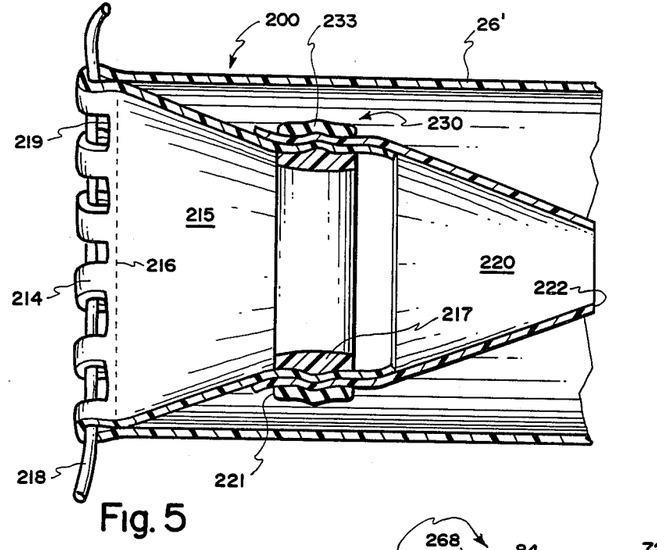
FIG. 5 is a fragmentary cross-section of the proximal end of the second presently preferred hyperbaric oxygenation apparatus according to the present invention.

Reference is now made to FIG. 5, which illustrates another proximal end assembly, generally designated 200. Proximal end assembly 200 comprises the impervious hyperbaric oxygenation bag 26', identical to heretofore described bag 26, except as hereinafter indicated. Bag 26' is inwardly reversed upon itself and sealed or stitched to itself along line 216. Notches 219 are cut, as illustrated. Thus, a series of loops 214 through which a drawstring 218 is caused to pass are created.

The bag 26' inwardly beyond line 216 is gathered so as to present a truncated conical configuration at section 215. The distal end of the cone-shaped section 215 of the inwardly directed proximal end of the bag 26' is connected to the larger proximal end of a cone-shaped sleeve or cuff 220. As stated earlier the cuff 220 is formed of highly stretchable sealing material, such as latex rubber, designed to be sized for a particular use by cutting to form the blunt end 222 having a diametral size selected to snugly and sealingly fit the limb of the patient placed within the hyperbaric oxygenation bag 26', in the manner heretofore described.

The juncture between the small leading end 221 of the frustoconical end 215 of the bag 26' and the large end of the cuff 220 is made permanent by a rigid internal ring 217 sized so as to require the large end of the cuff 220 to be stretched over the end of the distal end of the frustoconical section 215 of the bag 26'. An elastic band 233 having an unstressed diameter less than the outside diameter of the band 217 is stretched and placed over the assembled proximal end of the cuff 220 to complete the compression joint 230.

When the hyperbaric oxygenation apparatus comprising hyperbaric oxygenation bag 26' is properly installed upon the limb of a patient for treatment, as heretofore described, the drawstring 218 is manually tied snugly and contiguously to the limb of the patient. Hence, the interior of the bag 26' will pulsatingly receive oxygen at predetermined intervals causing the positive pressure and oxygen level within the bag 26' to vary between predetermined maximum and minimum values thereby cyclically fully inflating the bag 26' at maximum positive pressure and partially deflating the bag 26' at minimum positive pressure.

Figure 6:
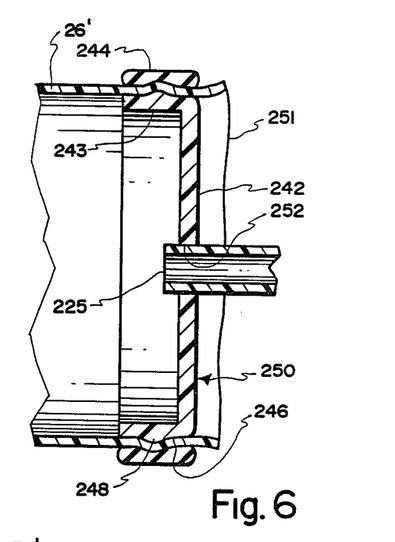
FIG. 6 is a fragmentary cross-section of the distal end of a second presently preferred hyperbaric oxygenation apparatus according to the present invention.

Reference is now made to FIG. 6, which illustrates a second embodiment for closing the distal end a hyperbaric oxygenation bag 26' in accordance with the principals of the present invention. Bag 26' is illustrated as terminating in an essentially blunt, cut edge 251. Disc-shaped closure 250 is inserted through the open end of the bag 26' at end 251. The outside diameter of the disc-shaped member 250 is illustrated as being substantially the same as the inside diameter of the tubular-shaped bag 26'. More specifically, the disc-shaped member 250 comprises a flat circular-shaped end wall 242 which extends transverse of the axis of the bag 26'. Wall 242 merges with an axially directed annular flange 243. Flange 243 and bottom wall 242 are illustrated as being of uniform thickness and essentially form a plug in the distal end of the tube 26'. The external surface of flange 243 at 246 comprises an outwardly directed annular rib 248. The disc-shaped member 250 also comprises an oxygen inlet/outlet port 225 integrally joined to the wall 242 in the sealed relation at aperture 252. Thus, in the embodiment of FIG. 6, the bag 26', unlike bag 26 as heretofore described, would not have an oxygen port in the wall thereof. The interior of the bag 26', in terms of influent and effluent oxygen, is serviced by the single port 225.

If desired, the bag 26' may be bonded or glued to the exterior surface 246. As illustrated, an elastic band 244, having an unstressed diameter less than the diameter of the flange 243, is stretched over the bag end 251 and the disc-shaped member 250 in radial alignment therewith and carefully released so as to compressively hold the closure 250 in sealed relation with the distal end of the bag 26' as illustrated in FIG. 6.

Figure 7:
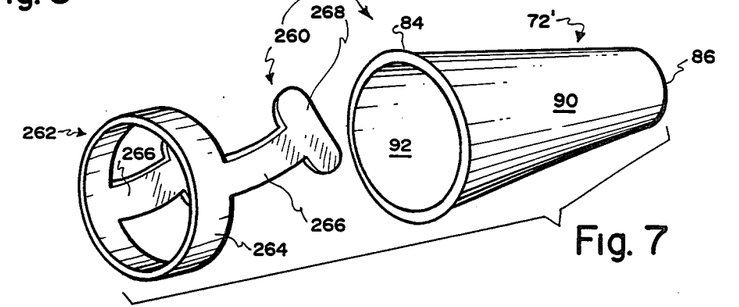
FIG. 7 is an exploded fragmentary perspective of a further sleeve-retainer and sleeve assembly forming part of the present invention.
Figures 8, 9:
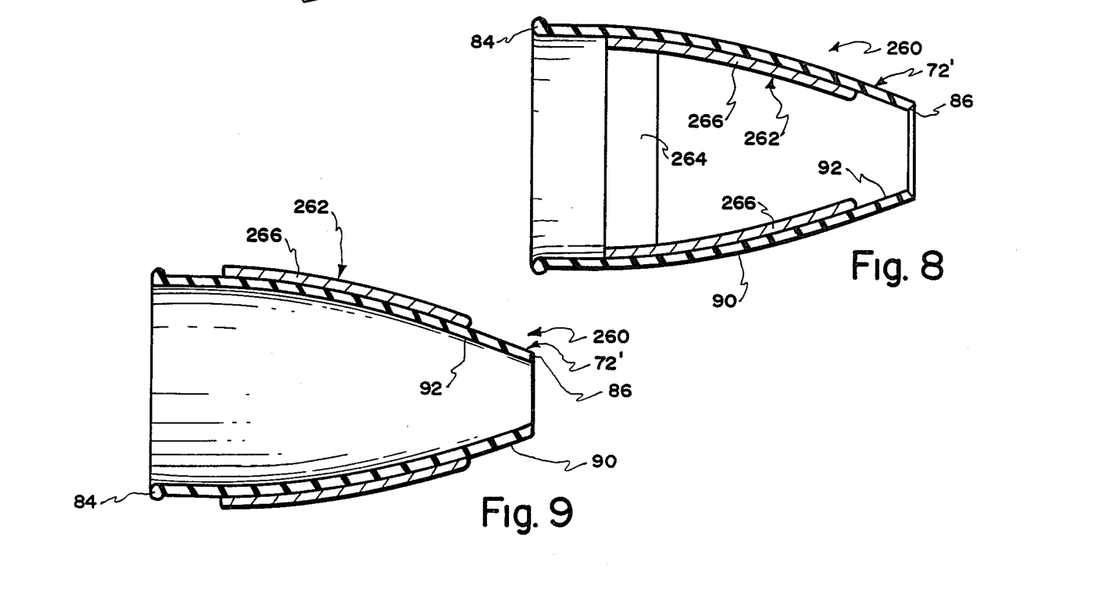
FIG. 8 is a fragmentary cross-sectional view of the assembled sleeve-retainer and sleeve embodiment of FIG. 7.
FIG. 9 is a fragmentary cross-sectional view similar to FIG. 8 illustrating the sleeve-retainer disposed outside of rather than inside of the sleeve.

Reference is now made to FIGS. 7 and 8 which illustrate an additional anti-blowout assembly, generally designated 260 according to the principles of the present invention. For ease of illustration, the bag and some of the proximal end assembly have been removed for purposes of clarity. It should also be understood that the anti-blowout mechanism 260 is used at the proximal end of a hyperbaric oxygenation apparatus of the type heretofore described. The assembly 260 is illustrated as comprising a sleeve or cuff 72' identical to the cuff 72 heretofore described except the pockets 85 are removed. No further description of sleeve 72' is believed to be necessary.

The assembly 260 also comprises the bracket, generally designated 262. The bracket 262 is preferably formed of rigid noncorrosive metal or plastic. The bracket 262 comprises an annular ring or band 264 of uniform thickness throughout defining uniform inside and outside diameters. The axial length of the ring 264 is relatively short. Integral with the ring at 264 are two opposed forwardly projecting inwardly converging struts or arms 266, which are illustrated as containing a slight curvature. Each arm 266 terminates in an enlarged foot 268. By placing the bracket 262 snugly within the interior of the sleeve 72' the ring 264 is sized so that it comes to rest within the proximal exterior of the sleeve 72' as illustrated in FIG. 8. Thus, when assembly 260 forms an integral part of the proximal end assembly of the present invention, as heretofore described, inversion of the sleeve 72' is prevented by the internal reinforcement supplied by the bracket 262, primarily at fingers 266.

In reference to FIG. 9, by correctly sizing the bracket 226 and the sleeve 72' the sleeve may be placed inside of the bracket 262 and secured thereto by adhesive or any other suitable connector to similarly prevent sleeve or cuff inversion or blowout.

Figure 10:
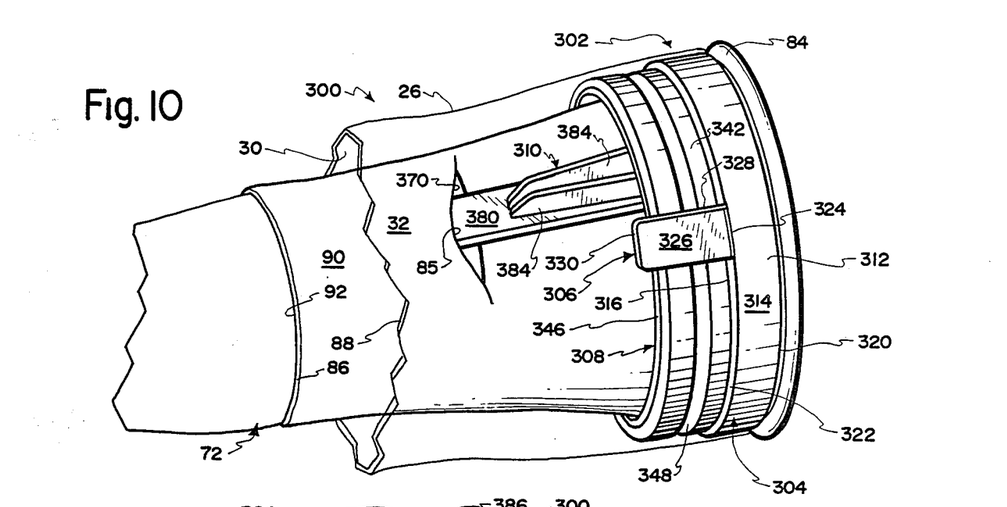
FIG. 10 is a fragmentary perspective of a further embodiment of the present invention.
Figures 11, 12:
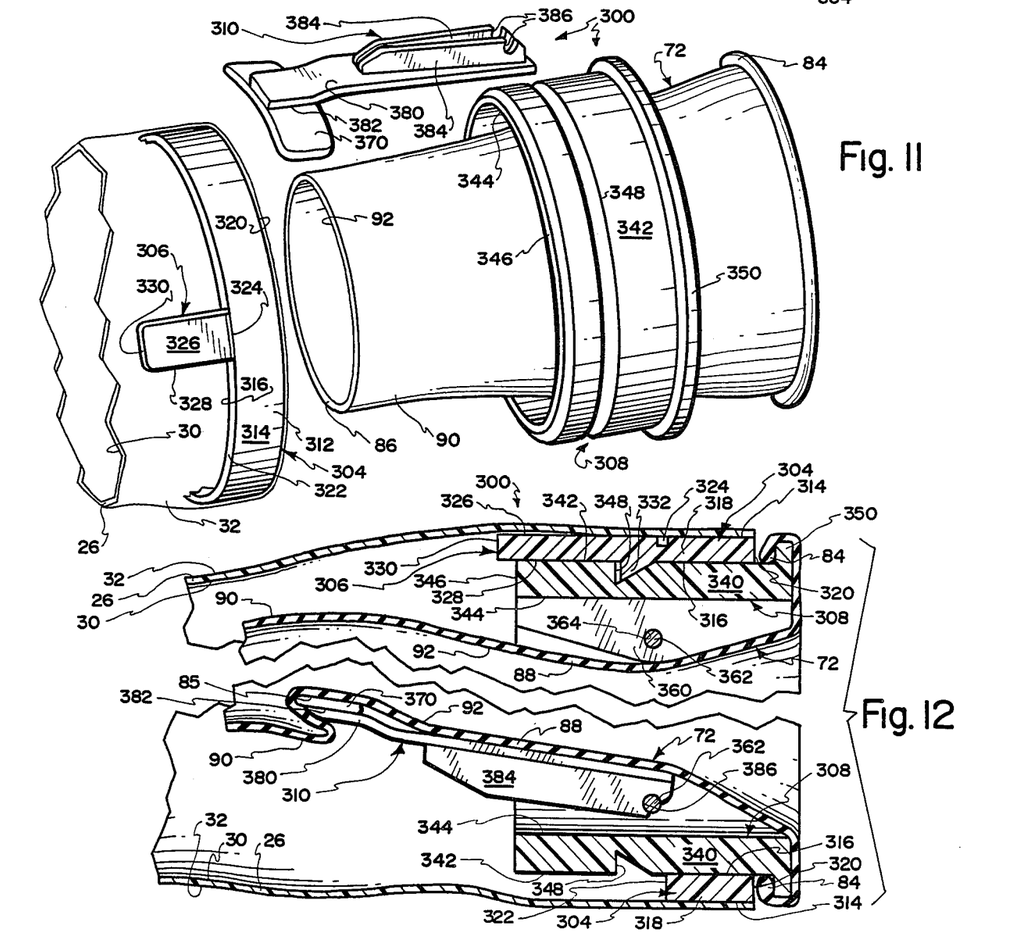
FIG. 11 is a fragmentary exploded perspective of the embodiment of FIG. 10.
FIG. 12 is a longitudinal cross-section of the embodiment of FIG. 10.

Reference is now made to FIGS. 10-12, which illustrate a further presently preferred hyperbaric oxygenation chamber apparatus, generally designated 300. The apparatus 300 may comprise any appropriate distal end closure configuration including the distal end closure configurations heretofore described in this specification. The apparatus 300 comprises the heretofore described bag 26 and a proximal end assembly, generally designated 302. Proximal end assembly 302 comprises the heretofore described sleeve 72. The proximal end assembly 302 also comprises a secondary collar or ring structure, generally designated 304, which collar comprises a plurality of forwardly directed flexible cantilevered latch fingers, each of which is generally designated 306. The proximal end assembly 302 also comprises a primary collar, generally designated 308, and anti-blowout sleeve restraining struts, each of which is generally designated 310.

The proximal end assembly 302 is intended to accomplish three primary objectives, i.e. (1) to prevent blowout or inversion of the sleeve or cuff 72 under positive internal pressure, (2) to prevent oxygen leakage and a corresponding loss of pressure between the sleeve 72 and the bag 26 at the proximal end which might otherwise occur by inadvertent forward displacement of the secondary collar or ring 304 from the primary collar 308 under positive pressure and (3) to provide a simplified proximal end assembly.

Secondary collar 304 comprises a ring 312 which is of uniform essentially rectangular cross-section (FIG. 12). Ring 312 comprises an exterior cylindrical surface 314, an interior cylindrical surface 316 and an annular wall 318. The ring 312 comprises a blunt transverse trailing edge 320 and a forward edge 322. The interior diameter at surface 316 is selected so that the secondary collar 304 is snugly slip fit upon primary collar 308, in a manner hereinafter more fully described. The outside diameter of the secondary collar 304 at surface 314 is selected to be substantially the same as the inside diameter of the sleeve bag 26. The proximal end of the sleeve 26 is secured to the surface 314 by use of a suitable bonding agent, adhesive or the like so as to create a hermetic seal therebetween. The leading edge 322 is interrupted, in the illustrated embodiment, by three forwardly extending latch fingers 306 placed at 120 degree intervals along the secondary collar 304. Each latch finger 306 is integral with the ring 312 and extends parallel to but offset from the axial center line of the apparatus 300.

Each latch finger 306 extends in a forward direction a distance illustrated as being slightly greater than the longitudinal dimension of the ring 312. The union site between each finger 306 and the ring 312 comprises a notch 324 (FIG. 12). This accommodates a retention of linearity on the part of each finger 306 in an unstressed latched state, that allows the medical attendant to lift each finger 306 through the bag 26 to accommodate unlatching when disassembly is desired.

Each latch finger 306 is essentially rectangular in its configuration and comprises a top surface 326, a bottom surface 328 and a continuous edge 330. The bottom surface 328 is interrupted by a latching barb 332, sized and shaped to be received and retained in an annular notch in the primary collar 308 as hereinafter more fully explained.

The primary collar 308 has an axial or longitudinal dimension substantially greater than the longitudinal dimension of the secondary collar 304. In cross-section, the primary collar 308 is generally L-shaped in its configuration and is annularly disposed at the proximal end of the apparatus 300. The primary collar 308 comprises a main annular wall 340 which is generally of uniform thickness defined by an outside cylindrical surface 342 and an inside cylindrical surface 344. The annular wall 340 terminates in a blunt leading edge 346.

The diameter of surface 342 is substantially the same as the inside diameter of ring 312 at surface 316 so that surfaces 342 and 316 are essentially contiguous and form a hermetic seal therebetween when assembled. The outside cylindrical surface 342 is interrupted by an annular notch 348 which is sized, located and shaped to receive the barb 332 of each latch finger 306, when the assembly 302 is fully assembled as illustrated in FIG. 12. Thus, the radial is extending, contiguously abutting surfaces of each barb 332 and the annular notch 348, respectively, will prevent forward displacement of the secondary collar 304 relative to the primary collar 308 during operation of the apparatus 300.

The wall 340 is integral with a radially extending flange 350, located at the trailing end of the assembly 302. The flange 350 is essentially rectangular in cross-sectional configuration and annularly extends through 360 degrees. The flange 350 is located so that it is spaced from the edge 320 of the secondary collar 304 by a short distance sufficient to accommodate placement of the lip 84 of the resilient sleeve 72, as hereinafter more fully explained. The flange wall 350 extends radially, in the illustrated assembled configuration, a distance slightly beyond the radial location of the surface 314 of the secondary collar 304.

Preferably, with the components of the asembly 302 fully disassembled, the sleeve or cuff 72 is radially stretched and rolled over or inverted upon the trailing end of the primary collar 308 so that the lip 84 of the resilient cuff 72 is placed into the position illustrated in FIG. 12 adjacent flange 350. In this position, the diameter of the lip 84 has been substantially enlarged as has the adjacent portion of the wall 88 of the resilient cuff 72. Accordingly, the trailing end of the sleeve 72 exerts a compressive force upon the collar 308 at flange 350, which retains the trailing end of the sleeve 72 in the assembled position, with the lip 82 resting between the flange 350 and the edge 320 of the secondary collar 304. Preferably, the secondary collar 304, with the trailing end of the bag 26 hermetically sealed thereto as explained earlier, is axially displaced over the outside surface 342 of the primary collar 308 until the barbs 332 of the fingers 306 latch into the annular groove 348. Thus, inadvertent separation of the secondary collar 304 from the primary collar 308 as well as a loss of pressure between the bag 26 and the sleeve 72 are prevented.

A plurality of ring mounting plates 360 are integrally secured by a suitable bonding agent, adhesive or the like to the inside annular surface 344 of the primary collar 308 (FIG. 12). Preferably, each mounting plate 360 is of uniform thickness and of the shape illustrated in FIG. 12. The radial dimension of each mounting plate 360 must be relatively small. Each mounting plate 360 may not have sharp edges which would otherwise cut and disable the cuff 72. The purpose of the mounting plates 360, which are located at a plurality of radial positions, is to secure an annular ring 362, which ring passes through and is retained in aperture 364 in each mounting plate 360. The surface of ring 362 is exposed and accessible between each mounting plate 360 to releasably receive the struts 310, which prevent blowout or inversion of the sleeve or cuff 72.

The struts 310 are designed to perform the same function as heretofore described in respect to struts 78, but are configured somewhat differently. Each strut 310 has a wide foot or shoe 370 shaped substantially the same as shoe or foot 160 of each strut 78. The shoe or foot 370 is transversely arcuate and comprises a wall of uniform thickness which is substantially greater in its transverse dimension than any other portion of the strut 310. Each strut 310 illustrates the foot 370 as being fabricated separate from the load-transferring stem 380 thereof. Each associated foot 370 and stem 380 are joined at site 382 by use of a suitable bonding agent, adhesive or the like. Both the foot 370 and the stem 380 are preferably formed of a shape retaining rigid plastic material. The stem 380 is divergently increased in its width from front to back and is reinforced by two ribs 384. Each rib 384 is integral with its associated stem 380, being either formed as one piece therewith or by use of a suitable bonding agent, adhesive or the like. The ribs 384 are each provided with a keyhole aperture 386. The two keyhole slots 386 of each strut 310 are transversely aligned and are sized and shaped so as to accommodate force-fitting thereof onto and manual removal from the exposed wire ring 362. Thus, each strut 310 is assembled releasably into the configuration illustrated in FIG. 12. Consequently, the struts 310 collectively exert both an inwardly-directed radial force and a longitudinal force from back to front upon the sleeve or cuff 72, when assembled so that the foot 370 of each strut 310 is placed in one of the pockets 85 in the sleeve 72, with the keyhole slots 386 force-fit upon the wire 362. See FIG. 12.

The invention may be embodied in other specific forms without department from the spirit or essential characteristics thereof. The present embodiments, are, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by U.S. Letters Patent is:

1. A hyperbaric oxgenation bag assembly comprising:
   an elongated collapsible disposable bag formed of impervious inflatable synthetic resinous material, the bag comprising a hollow interior sized to comfortably receive a limb of a patient and of sufficient strength to independently withstand the pressure stress imposed during oxygenation;
   means hermetically closing the distal end of the bag;
   oxygen input means by which oxygen under positive pressure delivered to the assembly is introduced into the hollow interior of the bag to oxygenate the limb;
   proximal end structure adapted to surround the limb, the proximal end structure comprising elastomeric sleeve means disposed within the proximal end of the bag adapted to compressively engage the limb of the patient so as to hermetically seal the proximal end of the bag and load transferring means forming part of the proximal end structure retaining the sleeve within the bag in said compressive position against loss of said hermetic seal due to sleeve displacement under force of said positive pressure;
   the proximal end structure further comprising rigid collar means loosely surrounding the limb and said retaining means further comprising a plurality of separate struts each comprising a leading end and a trailing end and each diagonally interposed between the rigid collar means and the sleeve means collectively exerting forces upon the sleeve means counter to said positive pressure introduced within the bag to prevent inversion and blowout of the sleeve means, the trailing end of each strut transferring forces to the rigid collar means across clip means releasably connecting the trailing end of each strut to the collar means.

2. A hyperbaric oxygenation bag assembly comprising:
   an elongated collapsible disposable bag formed of impervious inflatable synthetic resinous material, the bag comprising a hollow interior sized to comfortably receive a limb of a patient and of sufficient strength to independently withstand the pressure stress imposed during oxygenation;
   means hermetically closing the distal end of the bag;
   oxygen input means by which oxygen under positive pressure delivered to the assembly is introduced into the hollow interior of the bag to oxygenate the limb;
   proximal end structure adapted to surround the limb, the proximal end structure comprising elastomeric sleeve means disposed within the proximal end of the bag adapted to compressively engage the limb of the patient so as to hermetically seal the proximal end of the bag and load transferring means forming part of the proximal end structure retaining the sleeve within the bag in said compressive position against loss of said hermetic seal due to sleeve displacement under force of said positive pressure;
   the proximal end structure further comprising rigid collar means loosely surrounding the limb and said retaining means further comprising a plurality of separate struts each comprising a leading end and a trailing end and each diagonally interposed between the rigid collar means and the sleeve means collectively exerting forces upon the sleeve means counter to said positive pressure introduced within the bag to prevent inversion and blowout of the sleeve means, the leading end of each strut being secured in a pocket comprising part of the sleeve means.

3. A hyperbaric oxygenation bag assembly comprising:
   an elongated collapsible disposable bag formed of impervious inflatable synthetic resinous material, the bag comprising a hollow interior sized to comfortably receive a limb of a patient and of sufficient strength to independently withstand the pressure stress imposed during oxygenation;
   means hermetically closing the distal end of the bag;
   oxygen input means by which oxygen under positive pressure delivered to the assembly is introduced into the hollow interior of the bag to oxygenate the limb;
   proximal end structure adapted to surround the limb, the proximal end structure comprising elastomeric sleeve means disposed within the proximal end of the bag adapted to compressively engage the limb of the patient so as to hermetically seal the proximal end of the bag and load transferring means forming part of the proximal end structure retaining the sleeve within the bag in said compressive position against loss of said hermetic seal due to sleeve displacement under force of said positive pressure;
   the proximal end structure further comprising rigid collar means loosely surrounding the limb and said retaining means further comprising a plurality of separate struts diagonally interposed between the rigid collar means and the sleeve means collectively exerting forces upon the sleeve means counter to said positive pressure introduced within the bag to prevent inversion and blowout of the sleeve means, the rigid collar means comprising a first inner collar to which the proximal end of the bag is integrally attached, a second intermediate collar by which the proximal end of the sleeve means are compressively retained and within which the first inner collar is force-fit and exterior collar clamp means which, when closed, radially compressively hold the expanded end of the sleeve means and the intermediate collar to integrally unite the rigid collar means against inadvertent separation.

* * * * *